US00RE37024E

(19) United States
(12) Reissued Patent
Brust et al.

(10) Patent Number: US RE37,024 E
(45) **Date of Reissued Patent: *Jan. 16, 2001**

(54) ENDOSCOPIC LITHOTRIPSY SYSTEM

(75) Inventors: Thomas E. Brust, Eden Prairie; Timothy J. Ley, Minneapolis, both of MN (US)

(73) Assignee: Boston Scientific Corporation, Natick, MA (US)

( * ) Notice: This patent issued on a continued prosecution application filed under 37 CFR 1.53(d), and is subject to the twenty year patent term provisions of 35 U.S.C. 154(a)(2).

(21) Appl. No.: 08/928,400

(22) Filed: Sep. 12, 1997

Related U.S. Patent Documents

Reissue of:
(64) Patent No.: 5,449,363
Issued: Sep. 12, 1995
Appl. No.: 08/239,040
Filed: May 6, 1994

(51) Int. Cl.[7] ..... A61B 17/22
(52) U.S. Cl. ..... 606/128; 606/127
(58) Field of Search ..... 606/1, 127, 128, 606/167–173, 159, 185, 184; 417/397–399

(56) References Cited

U.S. PATENT DOCUMENTS

| | | | |
|---|---|---|---|
| 2,227,727 | 1/1941 | Leggiadro | 606/128 |
| 2,740,406 | 4/1956 | Tofflemire . | |
| 3,447,476 | 6/1969 | Farris . | |
| 3,543,590 | 12/1970 | Bergendal et al. . | |
| 3,823,717 | 7/1974 | Pohlman et al. . | |
| 3,890,977 | 6/1975 | Wilson . | |
| 4,030,063 | 6/1977 | Wallen . | |
| 4,095,667 | 6/1978 | Mahig et al. . | |
| 4,227,532 | 10/1980 | Bluhm et al. . | |
| 4,474,180 | 10/1984 | Angulo . | |
| 4,533,411 | 8/1985 | Melton . | |
| 4,609,368 | 9/1986 | Dotson, Jr. . | |
| 4,651,833 | 3/1987 | Karpf et al. . | |
| 4,654,092 | 3/1987 | Melton . | |
| 4,660,573 | 4/1987 | Brumbach . | |
| 4,664,112 | 5/1987 | Kensey et al. . | |
| 4,681,106 | 7/1987 | Kensey et al. . | |
| 4,692,139 | 9/1987 | Stiles . | |
| 4,727,875 | 3/1988 | Dory . | |
| 4,748,971 | 6/1988 | Borodulin et al. . | |
| 4,811,735 | 3/1989 | Nash et al. . | |
| 4,907,572 | 3/1990 | Borodulin et al. . | |
| 4,920,954 | 5/1990 | Alliger et al. . | |
| 4,936,845 | 6/1990 | Stevens . | |
| 5,156,143 | 10/1992 | Bocquet et al. . | |
| 5,160,336 | 11/1992 | Favre | 606/128 |
| 5,176,688 | 1/1993 | Narayan et al. | 606/128 |
| 5,190,546 | 3/1993 | Jervis | 606/78 |
| 5,197,968 | 3/1993 | Clement . | |
| 5,234,451 | 8/1993 | Osypka . | |
| 5,267,954 | 12/1993 | Nita | 604/22 |
| 5,382,228 | 1/1995 | Nita et al. | 604/22 |
| 5,425,735 | 6/1995 | Rosen et al. | 606/128 |
| 5,540,702 * | 7/1996 | Walz | 606/128 |
| 5,626,593 | 5/1997 | Imran | 606/159 |
| 5,722,980 * | 3/1998 | Schulz et al. | 606/128 |

* cited by examiner

*Primary Examiner*—Glenn K. Dawson
(74) *Attorney, Agent, or Firm*—Testa, Hurwitz & Thibeault, LLP

(57) ABSTRACT

An endoscopic lithotriptor including an elongated, flexible stone impacting member in the form of a wire whose distal end is brought against a stone to be broken and whose proximal end is adapted to be periodically struck by a hammer element. The hammer element is pneumatically driven by a linear jet of air causing it to swing through an arc about a pivot to impact an anvil affixed to the wire and oriented tangentially to the arc swept out by the hammer. The pneumatic chamber structure in which the hammer is pivotally mounted is designed to maximize the angular velocity reached by the hammer before impacting the anvil.

49 Claims, 2 Drawing Sheets

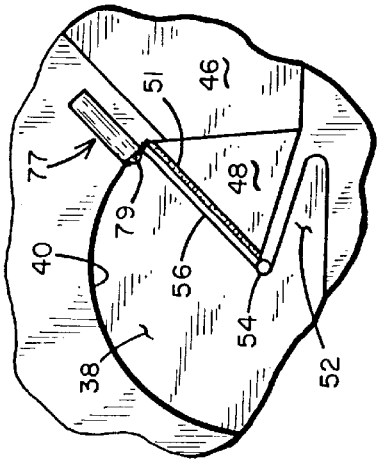
Fig. 2b
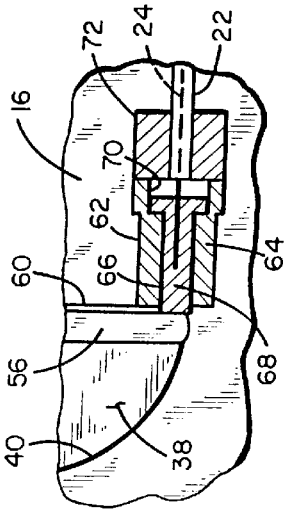
Fig. 2a
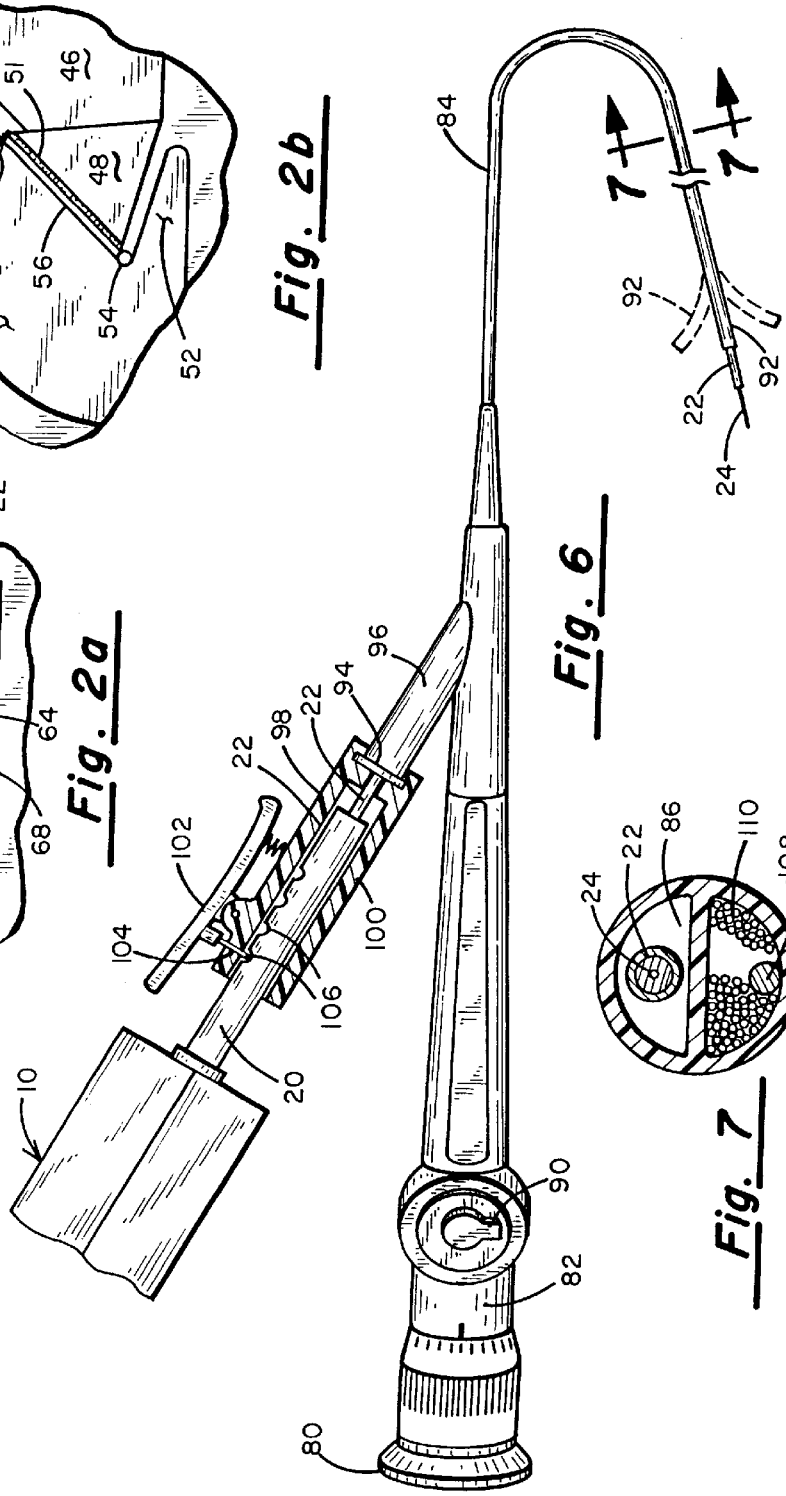
Fig. 6
Fig. 7

ENDOSCOPIC LITHOTRIPSY SYSTEM

Matter enclosed in heavy brackets [ ] appears in the original patent but forms no part of this reissue specification; matter printed in italics indicates the additions made by reissue.

BACKGROUND OF THE INVENTION

I. Field of the Invention

This invention relates generally to a lithotripsy device for breaking stones in the urinary tract or gall bladder, and more particularly to such a device having an elongated flexible stone impacting member designed to be passed through the working lumen of a steerable endoscope for applying a breaking force to renal or gall bladder calculi (stones) to mechanically break them to a size that can be more readily passed.

II. Discussion of the Prior Art

Over the past 15 years or so, the management of renal stones in the urinary tract has undergone radical change. In many instances, in the late 70's, open surgical removal was the principal mode of treatment for urolithiasis and cholecystolithiasis. In about 1980, percutaneous techniques, ureteroscopy and extracorporeal shock wave lithotripsy (ESWL) began to be used by urologists to successfully treat patients with renal calculus (stones). During the 1980's there have been a significant number of technical advances in the use of ESWL. Nonetheless, there still remains a need for endoscopic treatment of ureteral and renal calculi using ureteroscopy or percutaneous nephrolithotripsy, depending upon the location of the stone, its size and composition.

Various methods of endoscopic stone fragmentation have been discussed in the literature. In a paper by Reuter, et al., entitled "Electronic Lithotripsy of Utereal Calculi" published in the Journal of Urology in 1973, there is described an electrohydraulic lithotrite in which a spark induced shock wave travels through a fluid medium to the calculus to be fragmented. Electrohydraulic lithotripsy, however, is considered by some authors to be the most dangerous type to use.

There is also a laser device used in the endoscopic treatment of patients having renal stones. Here, a flexible or semi-rigid endoscope is used to transmit laser energy to the stone to be fragmented. However, it has been found that while laser probes are smaller in diameter and more readily insertable into the urinary tract, they do not have difficulty in fragmenting dense, poorly fragile calculi, such as calcium oxalate, monohydrate or cystine stones. Moreover, laser systems tend to be very costly, limiting their availability to major medical centers.

In about 1990, a pneumatically driven lithotrite referred to as the "Swiss Lithoclast" has been used and reported on by a number of urologists. The device in question is more particularly described in the Favre U.S. Pat. No. 5,160,336. It includes an elongated wire having an anvil on one end thereof which acts as a wave guide to transmit shock waves, created by a pneumatically driven bullet-like projectile striking the anvil, to a stone to be fragmented. The wave guide is adapted to be inserted through the working lumen of an endoscope for accurate positioning of the distal end thereof against the stone to be reduced.

There still remains a need for a more efficient endoscopic lithotripsy device for treating difficult stones, which are located in areas of the body that are hard to reach. Such a system must be capable of delivering high energy impacts while still capable of operating within the working lumen of small diameter flexible, steerable endoscopes.

It is accordingly a principal object of the present invention to provide a new and improved endoscopic lithotriptor.

Another object of the invention is to provide an endoscopic lithotriptor having a highly flexible stone impacting member, capable of passing through the lumen of an endoscope such as an ureteroscope or a nephroscope of conventional design.

Still another object of the invention is to provide a lithotriptor device capable of delivering a greater blow to a stone to more effectively fragment the stone.

Yet another object of the invention is to provide an improved pneumatic driven lithotriptor that is relatively small in size and attachable to an endoscope with which it is to be used without detracting from the ability of the urologist to view the site and manipulate the working end of the lithotriptor.

SUMMARY OF THE INVENTION

An intracorporeal lithotripsy device in accordance with the present invention comprises an elongated flexible, stone impacting member in the form of a metal wire having a distal end for engaging a calculated and a proximal end adapted to be struck by a hammer device. An elongated flexible sheath may be used to surround the stone impacting member over substantially its entire length and would have an outer diameter allowing its insertion through the working lumen of an endoscope. While the inclusion of the sheath has been found to enhance performance of the device, it is not essential to the effective operation of the present invention. Cooperating with the proximal end of the stone impacting member is a pivotally mounted mass comprising a swinging hammer device for repetitively applying an impact force to the proximal end of the wire. The hammer is pivotally mounted in a pneumatic chamber. Specifically, the hammer member is secured by a hinge pin within a cylindrical chamber and swings about the pin between a first "ready" position and a second "impacting" position in contact with the proximal end of an elongated wire stone impacting member. A means is provided for pneumatically driving the hammer member from its first position forcefully against the end of the wire in the second position to drive the proximal end of the wire against a stone to be divided and for returning the hammer member to its first position in anticipation of the administration of a subsequent blow to the wire.

The stone impacting member preferably comprises a stainless steel or Nitinol wire, each of which is capable of conforming to the shape of a flexible, steerable endoscope with which the lithotripsy device is to be used. The proximal end of the wire preferably has an anvil or striking surface affixed to it. As indicated above, the sheath surrounding the elongated wire is sized to pass through the working lumen of an endoscope and is preferably made from a lubricous plastic material, e.g., Teflon, so as to reduce frictional dampening of the wire even when the sheath and its enclosed wire stone impacting member are bent to some degree.

The cavity defining the pneumatic chamber is partitioned into three segments, the first being arcuate to accommodate the pivoting or swinging motion of the hammer member, the second being a large volume capacitance segment in fluid communication with the arcuate segment through a narrow slit located adjacent the first position and the third being a pressure relief segment in fluid communication with the arcuate segment proximate the second position. Surrounding the slit is a lip seal which cooperates with the hammer when in its "home" position. A source of pressurized air is introduced into the capacitance chamber while the pressure relief segment is exposed to the ambient or to a negative pressure. The lip seal prevents the arcuate segment from becoming pressurized prior to release of the hammer. When the hammer member is triggered, it thus sweeps through an arcuate path, forcefully striking the proximal end of the wire or the anvil member secured thereto and for translating the wire within its sheath and driving its distal end against the calculus to be fractured.

BRIEF DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 2(a) is an enlarged portion of the view of FIG. 2;

FIG. 2(b) is a different enlarged portion of the view of FIG. 2;

FIG. 6 is a perspective view of the intracorporeal lithotripsy device of the present invention used in combination with a flexible ureteroscope; and FIG. 7 is a cross-sectional view taken along the line 7—7 in FIG. 6.

DETAILED DESCRIPTION OF THE PREFERRED EMBODIMENT

Figure 1:
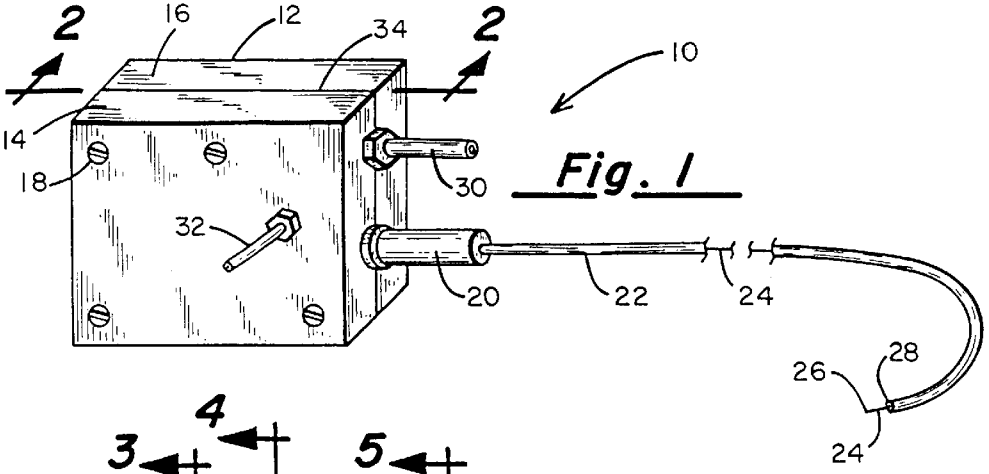
FIG. 1 is a perspective view of the intracorporeal lithotripsy device constructed in accordance with the present invention.

Referring to FIG. 1 there is indicated generally by numeral 10 a lithotriptor constructed in accordance with the present invention. While strictly speaking, a lithotrite is defined as a device for breaking renal stones, it is to be understood that the device of the present invention can be used to treat gallstones in a percutaneous procedure as well. It is seen to comprise a housing 12 comprising first and second housing halves 14 and 16 which are shown to be held together by screw fasteners 18. While the housing 12 is illustrated as being a generally rectangular block, it can be appreciated that the exterior of the housing may be shaped so as to provide a more streamlined and stylized appearance and can be fabricated from any of a number of medical grade plastics or metal.

Passing through a hub 20 forming a part of the housing 12 is an optional elongated tubular sheath member 22, preferably formed from a lubricous plastic material, such as Teflon or a polyimid plastic. A sheath fabricated from Nitinol affords superior flexibility properties and may also be used. The tubular sheath 22 surrounds a stone impacting member in the form of an elongated rod or wire 24 whose distal tip 26 extends slightly beyond the distal end 28 of the tubular sheath 22.

Also visible in the view of FIG. 1 is a tubular hose 30 which is adapted to be connected to a source of pressurized air (not shown) used to operate the lithotriptor 10. The housing 12 also has an air outlet port 32, the purpose of which will be further described as the specification continues.

Figure 2:
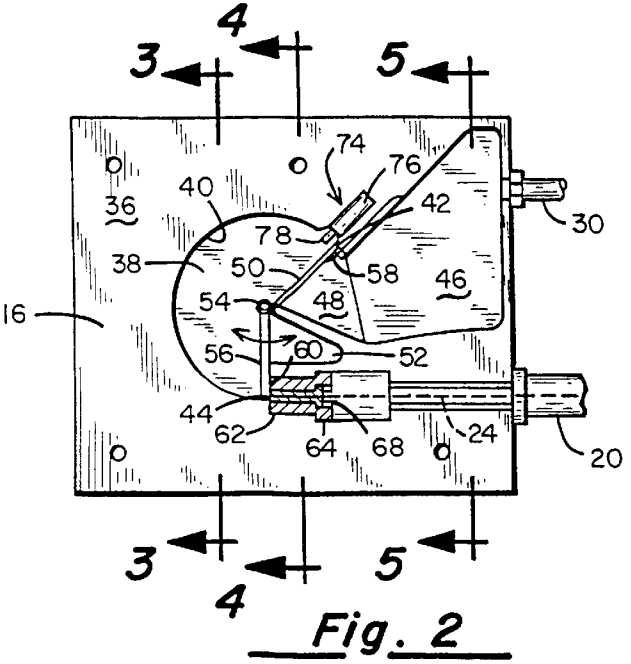
FIG. 2 is a sectional view taken along the line 2—2 in FIG. 1.
Figure 3:
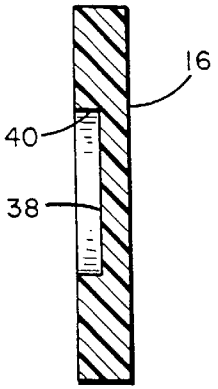
FIG. 3 is a cross-sectional view taken along the line 3—3 in FIG. 2.

Referring next to FIG. 2, which is a section taken along the parting line 34 between the housing halves 14 and 16, the internal parts of the lithotriptor 10 can be observed. Because the housing halves 14 and 16 are generally bilaterally symmetrical, it is only necessary to consider the internal constructional features of the housing half 16 shown in FIG. 2 to understand the internal structural features.

Figure 5:
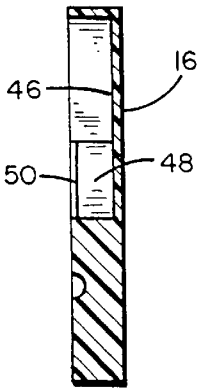
FIG. 5 is a cross-sectional view taken along the line 5—5 in FIG. 2.

Molded or otherwise formed into the face 36 of the housing half 16 is a cavity having a right circular cylindrical shape over a predetermined arc segment defining a generally circular wall surface 40 which extends from a first position termed the "ready position" indicated by numeral 42, to a second, "impacting position" 44. Also formed inwardly from the face 36 of the housing half 16 is a relatively large volume chamber 46 termed a capacitance chamber into which the pressurized air hose 30 enters. As can be observed from the cross-sectional view of FIG. 5, the capacitance chamber 46 terminates in an upwardly sloping segment 48 terminating in a narrow slit 50 when housing halves 14 and 16 are juxtaposed. Surrounding the slit 50 is a seal member 51, the function of which will be explained later on.

Also joined in fluid communication relationship with the arcuate portion 38 of the pneumatic chamber is a pressure relief segment 52. The outlet tube 32 exposes the pressure relief segment 52 to ambient pressure or to a vacuum, as desired.

Centrally disposed within the cylindrical segment 38 and extending perpendicularly to the floor of that chamber is a pivot pin 54 which passes through a sleeve bearing located in a bore formed at one end of a hammer member 56. The hammer member 56 is thus able to swing or rotate about the pin 54 as its center and the length of the hammer member 56 is such that only a small clearance fit exists between the free end thereof and the wall 40 with which it cooperates. A stop 58 is located proximate the first, ready position 42 of the hammer 56. Similarly, a stop 60 is provided at the second, impact position 44 of the hammer.

Figure 4:
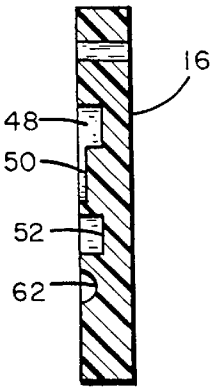
FIG. 4 is a cross-sectional view taken along the line 4—4 in FIG. 2.

Referring to FIGS. 2, 2(a) and 4, fitted into a groove 62 formed in the housing half 16 is a precisely machined anvil guide member 64 having a bore 66 therein for slidingly receiving an anvil member 68. The anvil member 68 is fixedly attached to the proximal end of the stone impacting wire 24 and its proximal end projects outwardly beyond the stop 60, allowing the anvil member 64 to be impacted by the hammer 56. The anvil guide member 62 has a counterbore 70 formed therein of a predetermined depth dimension that governs the extent of travel of the anvil member 68 in the distal direction when it is impacted by the hammer. A tubular metal sleeve 72 fits into a further semicircular groove formed in the housing halves 14 and 16 and abuts the anvil guide member 62, creating a surface against which the anvil member comes to rest at the end of its stroke.

With reference again to FIG. 2, there is identified by numeral 74 a hammer latching device or detent. It may comprise a microminiature pneumatic cylinder 76 having a piston rod 78 which is extensible and retractable relative to the cylinder 76. Alternatively, as shown in FIG. 2(b), it may comprise a conventional spring loaded ball detent 77 positioned so that the ball 79 engages the hammer 56 until a sufficiently high pressure sufficient to overcome the spring force that is applied to the ball. Assuming the use of a pneumatic cylinder, when the hammer member 56 is in its first or "ready" position against the stop 58, the pneumatic cylinder 76 may be actuated to extend the piston rod 78 to thereby block the hammer member 56 from moving as the capacitance chamber 46 becomes pressurized via pressurize are input line 30. The seal member 51 surrounding the slit 50 abuts the hammer member when in its latched condition, precluding the build-up of a back pressure in the arcuate chamber. When a predetermined pressure is developed within the capacitance chamber 46, the hammer detent 74 may be actuated to retract the piston rod 78, releasing the hammer. The built-up pressure causes a linear jet of air to exit the slit 50 through seal 51 and against the surface of the hammer 56, causing it to pivot about pin 54 with a high velocity and it ultimately strikes the anvil 68 to drive the stone impacting wire. The presence of the pressure relief chamber 52, coupled to the ambient via outlet 32, precludes the buildup of air ahead of the hammer during its travel, thus not appreciably dampening the angular velocity of the hammer 56 as it swings to strike the anvil.

Referring now to FIG. 6, there is shown the manner in which the lithotripsy device of the present invention may be used in conjunction with a flexible ureteroscope, such as the type manufactured and sold by Karl Storz, GmbH & Company. It may also be used with a variety of other commercially available endoscopies and is not limited solely for use with the Storz model. This endoscope is only one of several that can be used with the present invention. Such an endoscope includes an adjustable eyepiece 80 on the proximal end of a handle member 82. The handle member is on the proximal end of an elongated, flexible, multi-lumen tube 84 which may be in the range of from 8 cm to 122 cm in length. The outside diameter of the tube 84 may be on the order of 7.5 Fr. and, as shown in the cross-sectional view of FIG. 7, may have a working channel 86 running the full length thereof and accessible through the branch 88 of a Y connection on the handle 82. By manipulating the lever 90, the distal tip portion 92 of the ureteroscope may be deflected actively in two directions (120° up, and 170° down) as represented by the dotted lines to allow atraumatic access into any calyx of the kidney.

The lithotriptor device 10 of the present invention is adapted to be coupled to the Luer fitting 94 on a Y-branch 96 of the endoscope by means of an adapter 98 that allows adjustment of the amount of extension of the distal end of the lithotriptor beyond the distal end 92 of the endoscope. The adapter comprises a rod having a straight bore 100 formed longitudinally therein for receiving the portion 20 of the lithotriptor device therein. Pivotally joined to the adapter 98 is a thumb lever 102 having a pin 104 projecting from the undersurface thereof. The pin 104 is adapted to pass through a radial bore in the housing 98 and the end thereof is designed to mate with one of a series of longitudinally spaced recesses 106 formed in the nose portion 20 of the lithotriptor. Thus, when the thumb lever is depressed to lift the pin free of the recesses or detents, the nose 20 of the lithotriptor can be repositioned within the bore 100 and then when the lever 102 is again released, the pin will again secure the nose member 20 against movement.

The cross-sectional view of FIG. 7 shows an illumination optical fiber 108 and a plurality of image fibers 110 that lead from the optics of the eyepiece to an objective lens (not shown) disposed at the distal end 92 of the tube 84. In this fashion, internal cavities of the body can be illuminated and the illuminated image viewed, via the fiber-optic bundle, contained within the ureteroscope.

The outer sheath 22, containing the stone impacting wire 24, passes through the working lumen 86 with sufficient clearance that, if desired, a flushing liquid can be injected through the working lumen 86 to maintain the objective lens at the distal end of the fiber-optic bundle free of body fluids that might otherwise occlude the view.

In use in an intracorporeal procedure for resolving renal stones, the physician will advance the assembly of FIG. 6 through the urethra, the bladder and into the ureters while viewing the scene through the eyepiece 80 and manipulating the lever 90 to steer the distal end of the ureteroscope. When the distal end of the scope is positioned against a stone to be disintegrated, the distal impact tip 26 of the stone impacting member 24 is advanced out of the endoscope and placed against the stone. The physician will next press a control pedal (not shown) to supply pressurized air from a pneumatic control module to the capacitance chamber 46. When the pressure within the capacitance chamber has stabilized at a maximum desired value, the detent mechanism 74 is actuated to release the hammer and the pressure exerted by a burst of air exiting through the narrow slit 50 and seal 51 (FIG. 2(b)) will cause the hammer 56 to pivot or spin rapidly about the pivot pin 54, sweeping through the arcuate chamber 36 until it strikes the anvil 44 to generate the driving impact. The distal end of the wire 24 is driven against the stone to be fractured. The hammer can be returned to its ready or first position following a given impact by selectively pressurizing the pressure relief chamber 60, via tube 32, to pneumatically drive the hammer in its reverse direction until it reaches the stop 58 and is again latched by the detent device 74.

The lithotriptor 10 is preferably powered pneumatically from a remote source of gas pressure, such as a hospital air line or pressurized air supply. Alternatively, a bottle of compressed gas may readily be substituted where a suitable hospital air supply is unavailable. Disposed between the air supply and the tube 30 is a foot-pedal actuated control module including pneumatic switches which effectively form a pneumatic oscillator. The operating frequency thereof may be adjusted through the use of pneumatic restrictors and is a physician-adjustable parameter. Such a control unit is designed to alternatively pressurize the lines 30 and 32 to drive the hammer between its ready position, its impact position and back to its ready position.

The stone impacting wire 24 can be fabricated from stainless steel but a Nitinol alloy is preferred because of its superior flexibility properties. This allows the wire 24 to traverse the sheath or working lumen of the endoscope without significant dampening even when the ureteroscope and the sheath 22 surrounding the stone impacting wire 24 are nonlinear.

With no limitation intended because the dimensions of the sheath 22 and wire 24 are somewhat dependent upon the endoscope with which the lithotriptor system is used, it has been found that a wire of a diameter of 0.020 in. and slightly flattened at locations corresponding to the curved areas of the scope has been quite effective. The flattening has the beneficial effect of allowing the wire to navigate the bends in the endoscope without introducing unwanted frictional contract. Greater flexibility may also be introduced at predetermined locations along its length by laser cutting or electrical discharge machinery slits in the wire at the selected locations. It is also recognized that the wire can be made as a composite with a highly flexible wire segment, such as Nitinol wire, being used in the zones where the endoscope is designed to bend and stainless steel being used in the remainder of the impacting wire member. The overall length of the sheath and wire is, of course, also dependent upon the particular endoscope with which it is used. The gap between the head of the anvil and the stop member 72 may be such as to provide a stroke of about 0.080 in or less.

While not shown in the drawings, to ensure that the anvil 68 is returned to its home position after having been struck by the hammer, a jet of air may be introduced to act against the face of the anvil to move it as a piston within the guide member 64.

While the ureteroscope shown in FIG. 7 is intended to allow the lithotripsy device of the present invention to be used in an intracorporeal procedure, those skilled in the art can appreciate that with only minor modification, it may be used in carrying out a percutaneous procedure. In this regard, the length of the stone impacting member and its surrounding sheath is reduced and designed to fit through the working lumen of an endoscope specifically configured for carrying out the percutaneous procedure. Here, the endoscope may be rigid or semi-rigid rather than flexible.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A lithotripsy device comprising:

(a) an elongated, stone impacting member having a distal end for engaging a calculus and a proximal end;

(b) hammer means for repetitively applying an impact force to said stone impacting member, said hammer means including a chamber having a hammer member rotatably mounted therein and rotatable between a first ready position displaced from said proximal end of said stone impacting member and a second position in contact with said proximal end of said stone impacting member;

(c) means for driving said hammer member from said first ready position forcefully against said stone impacting member in said second position to drive said distal end of said stone impacting member against said calculus; and (d) means for returning said hammer member to said first ready position.

2. The lithotripsy device as in claim 1 wherein said chamber is a pneumatic chamber.

3. The lithotripsy device as in claim 2 and further including means for releasably restraining said hammer member in said first ready position until a desired pressure is built up in a portion of said pneumatic chamber.

4. The lithotripsy device of claim 3 wherein said pneumatic chamber comprises a block of material having a cavity formed therein, said cavity including an arcuate segment containing said rotatably mounted hammer member, a capacitance segment in fluid communication with said arcuate segment through a narrow slit formed at a juncture of said capacitance segment with said arcuate segment and located adjacent said hammer member when in said first ready position and a pressure relief segment in fluid communication with said arcuate segment located adjacent said hammer member when in said second position.

5. The lithotripsy device as in claim 4 and further including a seal member surrounding said narrow slit adapted to cooperate with said hammer member when said hammer member is in said first ready position.

6. The lithotripsy device as in claim 4 and further including a high pressure gas inlet communicating with said capacitance segment and a gas outlet communicating with said pressure relief segment.

7. The lithotripsy device as in claim 4 wherein said means for releasably restraining said hammer member comprises a pneumatic cylinder mounted in said block having a piston rod extendable and retractable relative to said pneumatic cylinder, said piston rod being disposed in a path of travel of said hammer member when said hammer member is in said first ready position and out of said path of travel when retracted.

8. The lithotripsy device as in claim 4 wherein said means for releasably restraining said hammer member comprises a spring-loaded ball detent mounted in said block, said ball engaging said hammer member when said hammer member is in said first ready position.

9. The lithotripsy device as in claim 4 wherein said stone impacting member has an outer diameter of a size capable of passing through a working lumen of one of a rigid endoscope and a flexible, steerable-tip endoscope when said block of material is coupled to a handle of the endoscope.

10. The lithotripsy device as in claim 4 and further including means for mounting said block of material to an endoscope, said means for mounting including means for adjusting an extent by which said distal end of said stone impacting member extends beyond a distal end of said endoscope.

11. The lithotripsy device as in claim 10 wherein said means for mounting includes means for releasably latching said block of material to said endoscope at any one of a plurality of positions.

12. The lithotripsy device as in claim 1 wherein said stone impacting member is a flexible metal wire.

13. The lithotripsy device as in claim 12 and further including an elongated flexible, sheath surrounding said flexible metal wire.

14. The lithotripsy device as in claim 13 wherein said sheath is made of material selected from a class including stainless steel, Nitinol, polyimid plastic and PTFE plastic.

15. The lithotripsy device as in claim 13 wherein said sheath has an outer diameter of a size capable of passing through a working lumen of one of a flexible steerable tip endoscope and a rigid endoscope.

16. The lithotripsy device as in claim 13 wherein said sheath has an outer diameter of a size capable of passing through a working lumen of one of a rigid endoscope and a flexible, steerable-tip endoscope when said block of material is coupled to a handle of the endoscope.

17. The lithotripsy device as in claim [4] *12* wherein said flexible metal wire is formed from a metal selected from a [class including] *group consisting of* stainless steel and [Nitinol] *shape memory alloy*.

18. The lithotripsy device as in claim 12 wherein said wire is in the range of from about 8 cm to 122 cm in length.

19. The lithotripsy device as in claim 1 and further including an anvil member affixed to said proximal end of said stone impacting member and means cooperating with said anvil member for limiting the extent of travel of said anvil member when impacted by said hammer member.

*20. The lithotripsy device according to claim 17 wherein said shape memory alloy is Nitinol.*

*21. A lithotripsy device comprising:*

*a flexible elongated stone impacting member having a distal end for contacting a calculus, and a proximal end;*

*a hammer for repetitively applying an impact force to the stone impacting member, rotatably mounted in a chamber and rotatable between a first position displaced from the proximal end of the stone impacting member and a second position in contact with the proximal end of the stone impacting member; and*

*a mechanism to drive the hammer from the first position into the second position and from the second position into the first position.*

*22. The lithotripsy device according to claim 21, wherein the flexible elongated stone impacting member is fabricated from one of stainless steel, Nitinol, and a combination of Nitinol and stainless steel.*

*23. The lithotripsy device according to claim 21, wherein the flexible elongated stone impacting member is detachable from the rest of the lithotripsy device.*

*24. The lithotripsy device according to claim 21, further comprising a flexible elongated tubular sheath surrounding the elongated stone impacting member.*

*25. The lithotripsy device according to claim 24, wherein the flexible elongated tubular sheath is formed from a lubricious material.*

*26. The lithotripsy device according to claim 24, wherein the flexible elongated tubular sheath is formed from a group consisting of stainless steel, polyimid plastic, PTFE plastic, and Nitinol.*

*27. The lithotripsy device according to claim 24, wherein the distal end of the flexible elongated stone impacting member extends beyond a distal end of the flexible elongated tubular sheath.*

*28. The lithotripsy device according to claim 21, wherein said mechanism comprises a pneumatic power source.*

*29. A method of impacting stones in the body using a lithotripsy device, the method comprising the steps of:*

*inserting an endoscope into an area of the body to be treated;*

*providing a driving force to a hammer rotatably mounted in a lithotripsy device, which causes the hammer to rotate and contact a flexible stone impacting member; and*

*repetitively providing a stone impacting force from the hammer to the flexible stone impacting member.*

*30. The method of impacting stones in the body according to claim 29, further comprising the step of advancing the endoscope through the urethra and into the ureters.*

*31. The method of impacting stones in the body according to claim 29, wherein said providing step comprises providing the driving force which comprises a pneumatic force.*

*32. The method of impacting stones in the body according to claim 29, wherein the endoscope is inserted percutaneously.*

*33. The method of impacting stones in the body according to claim 29, wherein the endoscope is inserted intracorporeally.*

*34. The method of impacting stones in the body according to claim 29, wherein the flexible stone impacting member is fabricated from one of stainless steel, Nitinol, and a combination of Nitinol and stainless steel.*

*35. The method of impacting stones in the body according to claim 29, wherein the flexible stone impacting member is detachable from the rest of the lithotripsy device.*

*36. A pneumatic lithotripsy device, comprising:*

*a flexible elongated stone impacting wire including a distal end for containing a calculus, and a proximal end, the flexible elongated stone impacting wire comprising a shape memory alloy and capable of being curved into a body lumen;*

*a housing comprising a hammer for repetitively applying an impact force to the stone impacting wire, the hammer including a chamber having a hammer member mounted therein and positionable between a first position displaced from the proximal end of the stone impacting wire and a second position in contact with the proximal end of the stone impacting wire;*

*a pneumatic hammer driver providing a driving force to place the hammer member in the first and second positions; and*

*a flexible elongated tubular sheath attached to said housing and surrounding at least a portion of the flexible elongated stone impacting wire.*

*37. The lithotripsy device of claim 36 wherein said shape memory alloy is Nitinol.*

*38. The lithotripsy device according to claim 36, wherein the flexible elongated stone impacting wire is detachable from the rest of the lithotripsy device.*

*39. The lithotripsy device according to claim 36, wherein the flexible elongated tubular sheath is formed from a lubricious material.*

*40. The lithotripsy device according to claim 36, wherein the flexible elongated tubular sheath is formed from a group consisting of stainless steel, polyimid plastic, PTFE plastic, and Nitinol.*

*41. The lithotripsy device according to claim 36, wherein the distal end of the flexible elongated stone impacting wire extends beyond a distal end of the flexible elongated tubular sheath.*

*42. The lithotripsy device of claim 36 wherein said stone impacting wire has a diameter of 0.020 inches.*

*43. The lithotripsy device of claim 36 wherein said stone impacting wire has portions which are flattened.*

*44. The device of claim 36 wherein said flexible elongated sheath comprises stainless steel and plastic.*

*45. A method of impacting stones in the body using a pneumatic lithotripsy device, comprising:*

*inserting an endoscope into an area of the body to be treated;*

*providing a pneumatic driving force to a hammer mounted in a housing of a lithotripsy device which causes the hammer to move from a first position displaced from the proximal end of a flexible elongated stone impacting wire to a second position in contact with the proximal end of the flexible elongated stone impacting wire; and*

*repetitively providing a stone impacting force from the hammer to the flexible elongated stone impacting wire which comprises a shape memory alloy and which contacts a stone to be treated, wherein the flexible elongated stone impacting wire extends through and is capable of being curved into a working lumen of the endoscope and at least a portion of the flexible elongated stone impacting wire is surrounded by a flexible elongated sheath attached to said housing.*

*46. The method of impacting stones in the body according to claim 43, further comprising the step of advancing the endoscope through the urethra and into the ureters after the endoscope is inserted into the body.*

*47. The method of impacting stones in the body according to claim 45, wherein the endoscope is inserted percutaneously.*

*48. The method of impacting stones in the body according to claim 45, wherein the endoscope is inserted intracorporeally.*

*49. The method of impacting stones in the body according to claim 43, wherein the flexible elongated stone impacting wire is detachable from the rest of the lithotripsy device.*

* * * * *